(12) United States Patent
Dhalla et al.

(10) Patent No.: US 12,089,897 B2
(45) Date of Patent: Sep. 17, 2024

(54) SYSTEMS AND METHODS FOR MULTIPLEXING AND ALTERNATING LIGHT OF DIFFERENT WAVELENGTHS IN AN OPHTHALMOSCOPE

(71) Applicant: Duke University, Durham, NC (US)

(72) Inventors: Al-Hafeez Dhalla, Durham, NC (US); Anthony Kuo, Durham, NC (US); Joseph Izatt, Durham, NC (US)

(73) Assignee: Duke University, Durham, NC (US)

( * ) Notice: Subject to any disclaimer, the term of this patent is extended or adjusted under 35 U.S.C. 154(b) by 490 days.

(21) Appl. No.: 17/610,535

(22) PCT Filed: Jun. 19, 2020

(86) PCT No.: PCT/US2020/038638
§ 371 (c)(1),
(2) Date: Nov. 11, 2021

(87) PCT Pub. No.: WO2020/257582
PCT Pub. Date: Dec. 24, 2020

(65) Prior Publication Data
US 2022/0240777 A1     Aug. 4, 2022

Related U.S. Application Data

(60) Provisional application No. 62/863,997, filed on Jun. 20, 2019.

(51) Int. Cl.
*A61B 3/12* (2006.01)
*A61B 1/00* (2006.01)
*A61B 1/07* (2006.01)

(52) U.S. Cl.
CPC ............ *A61B 3/12* (2013.01); *A61B 1/00172* (2013.01); *A61B 1/07* (2013.01)

(58) Field of Classification Search
CPC .......... A61B 3/12; A61B 1/00172; A61B 1/07
See application file for complete search history.

(56) References Cited

U.S. PATENT DOCUMENTS

| 6,341,865 B1 | 1/2002 | Muehlhoff et al. |
| 11,134,841 B2 | 10/2021 | Katashiba et al. |

(Continued)

FOREIGN PATENT DOCUMENTS

WO     2019044457 A1     3/2019

OTHER PUBLICATIONS

International Preliminary Report on Patentability and Written Opinion dated Dec. 21, 2021 in associated PCT International Application No. PCT/US2020/038638 (8 pages).

*Primary Examiner* — James C. Jones
(74) *Attorney, Agent, or Firm* — Olive Law Group, PLLC

(57) ABSTRACT

Systems and method for multiplexing and alternating light of different wavelengths in an ophthalmoscope are disclosed herein. According to an aspect, an imaging system includes an illumination system configured to generate and output light that alternates between at least two different wavelengths. The imaging system includes a multiplexer configured to receive the output light and to multiplex the light of different wavelengths onto a single optical channel. Further, the imaging system includes a scanning laser ophthalmoscope probe configured to operatively receive the multiplexed light, to apply the multiplexed light to a subject for imaging, and to receive light returning from the subject for generating an image of the subject.

45 Claims, 8 Drawing Sheets

(56) References Cited

U.S. PATENT DOCUMENTS

2009/0292168 A1 11/2009 Farr
2017/0273548 A1* 9/2017 Takata .................. G02B 23/26

* cited by examiner

SYSTEMS AND METHODS FOR MULTIPLEXING AND ALTERNATING LIGHT OF DIFFERENT WAVELENGTHS IN AN OPHTHALMOSCOPE

CROSS REFERENCE TO RELATED APPLICATION

This is a 371 national stage patent application which claims priority to PCT international patent application No. PCT/US2020/038638, filed Jun. 19, 2020, and titled SYSTEMS AND METHODS FOR MULTIPLEXING AND ALTERNATING LIGHT FOR DIFFERENT WAVELENGTHS IN AN OPHTHALMOSCOPE, which claims priority to U.S. Provisional Patent Application No. 62/863,997, filed Jun. 20, 2019, and titled SYSTEMS AND METHODS FOR POLYCHROMATIC POINT SCANNING IMAGING, the disclosures of which are incorporated herein by reference in their entireties.

FEDERALLY SPONSORED RESEARCH OR DEVELOPMENT

This invention was made with government support under Federal Grant No. 5R01EY024312, awarded by the National Eye Institute (NEI) of the National Institutes of Health (NIH), and under Federal Grant No. 5R21EY030270, awarded by NIH. The government has certain rights to this invention.

TECHNICAL FIELD

The presently disclosed subject matter relates generally to medical imaging. Particularly, the presently disclosed subject matter relates to systems and methods for multiplexing and alternating light of different wavelengths ophthalmoscope.

BACKGROUND

Confocal scanning laser ophthalmoscopy (CSLO) is a medical imaging modality that confers the ability to capture high resolution and high contrast images of the retina with emerging applications in screening for retinal disease. The technology is based on a more generalizable imaging approach called confocal scanning laser microscopy (CSLM). Polychromatic or "color" implementations of CSLO and CSLM employ complex and expensive system topologies that are not well suited for miniaturization (due to complexity) or commercialization for screening applications (due to cost). Although the term "laser" is used in the common name "scanning laser ophthalmoscope", alternatives to lasers, such as superluminescent diodes or supercontinuum sources, may be used as light sources for imaging.

Inertia limits the speed at which scanning mirrors can be driven, which in turn limits imaging frame rates in point scanning systems. These limits are exacerbated in low-cost and small footprint applications that employ micro-electro-mechanical system (MEMS) scanners or galvanometer scanners, as these scanners tend to have relatively low resonance frequencies. As a result, a single-channel point scanning imaging system employing a MEMS or galvanometer scanner have modest photoreceiver and digitization bandwidth requirements, leaving significant bandwidth headroom even when employing low-cost digitizers and photoreceivers. In view of the foregoing, there is an opportunity for improved techniques to provide CSLO systems that are more efficient, more easily scalable, and have a smaller footprint.

BRIEF DESCRIPTION OF THE DRAWINGS

Figure 1:
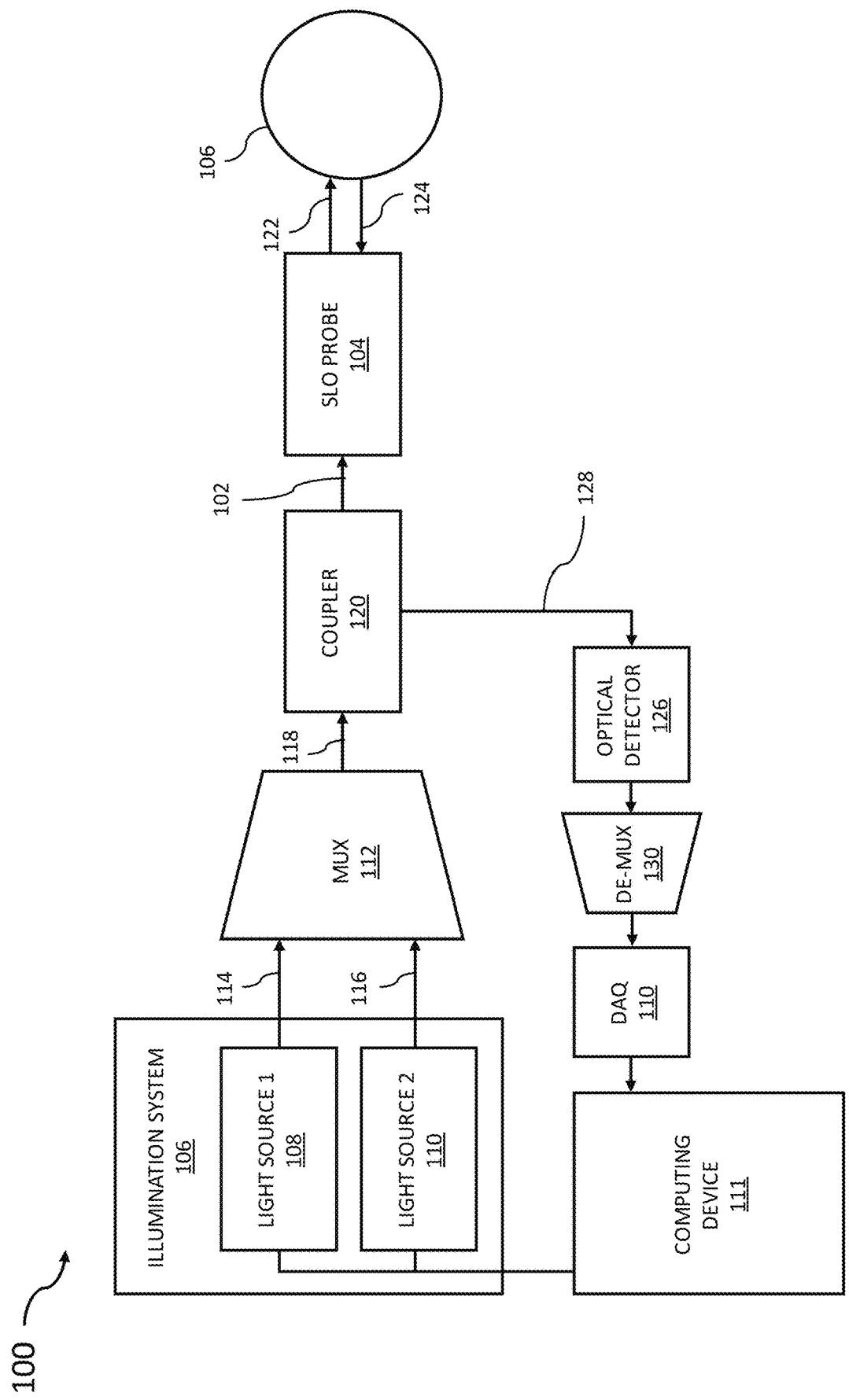
Figure 2:
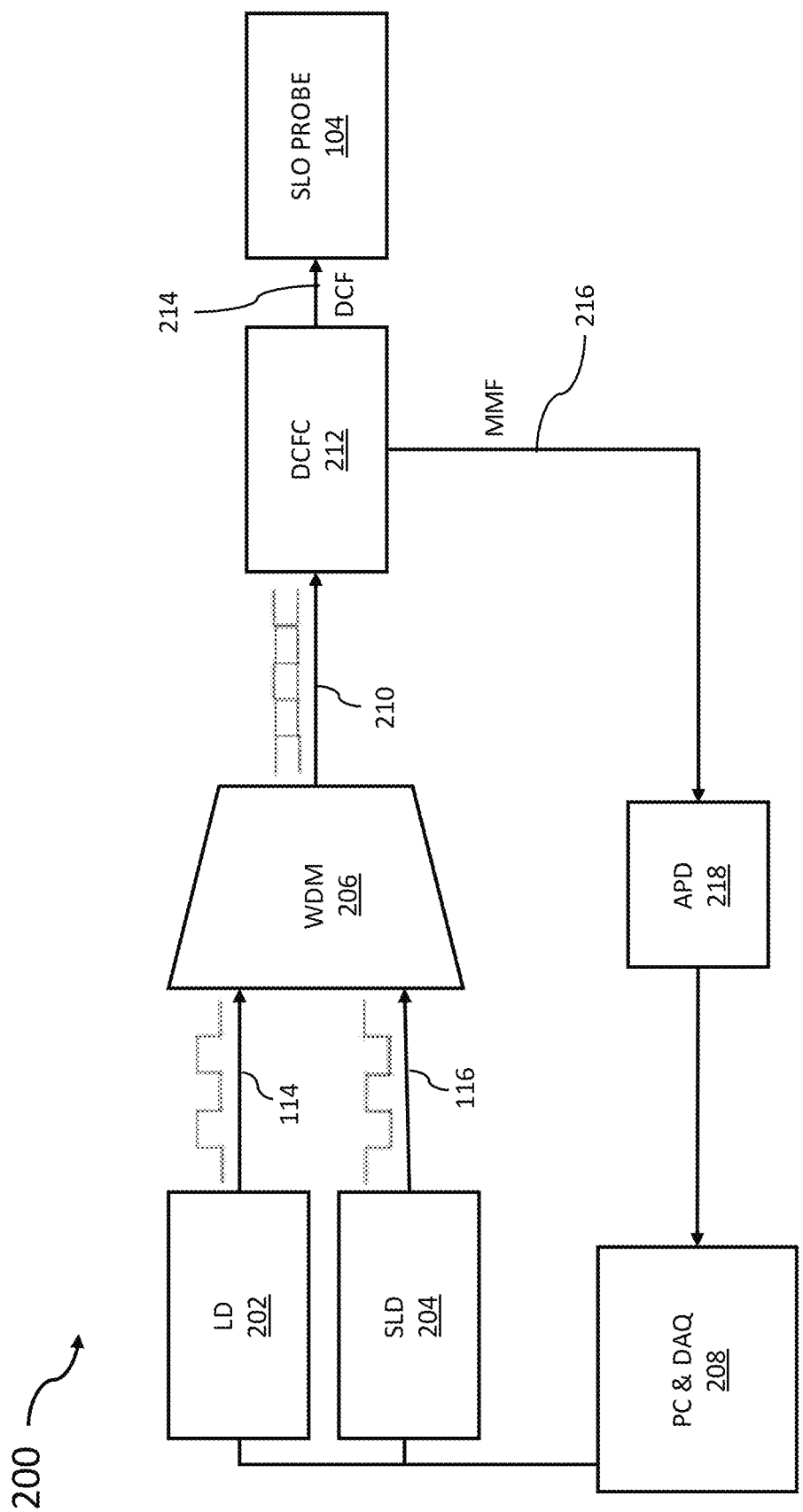
Figure 3:
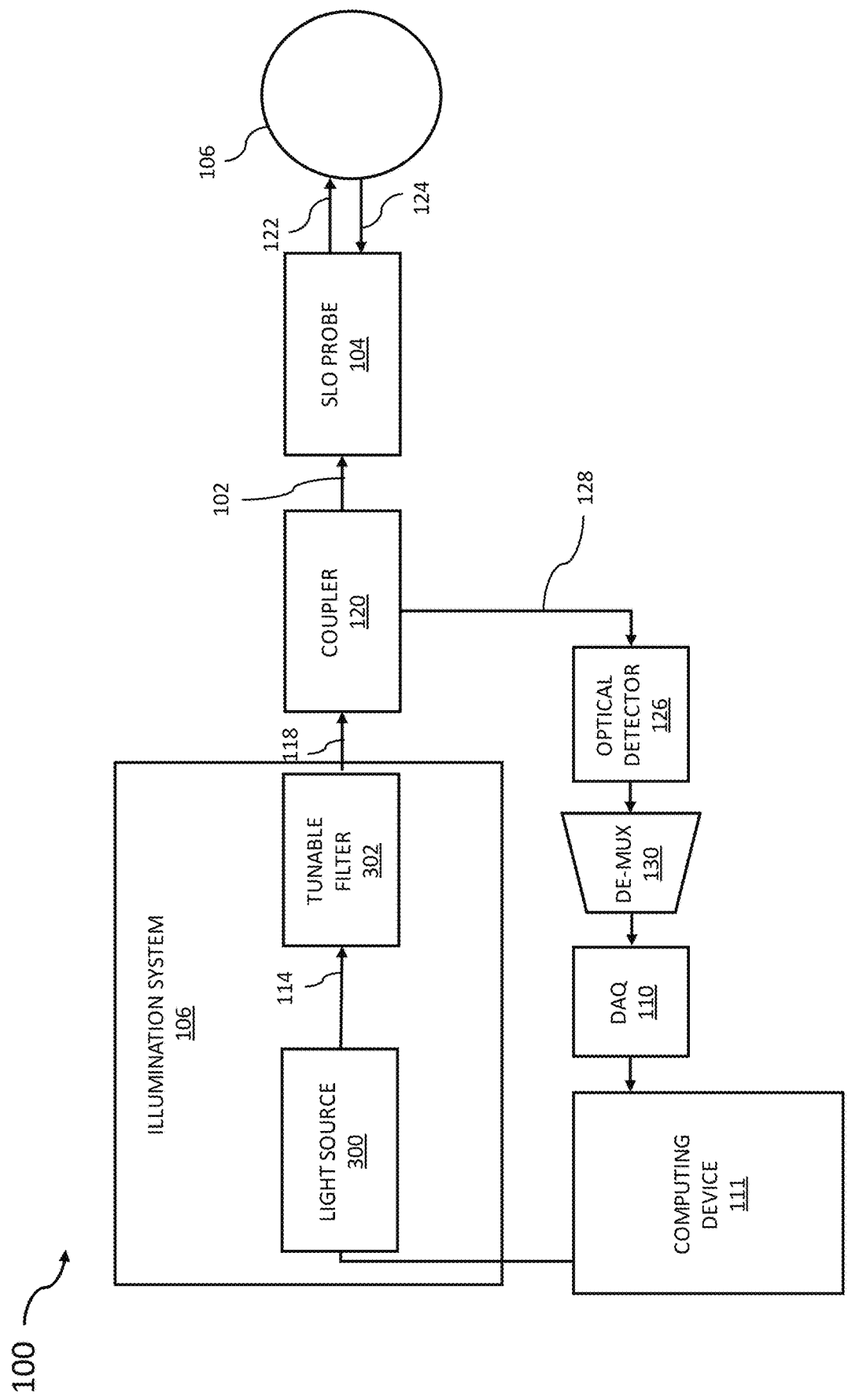
Figure 4:
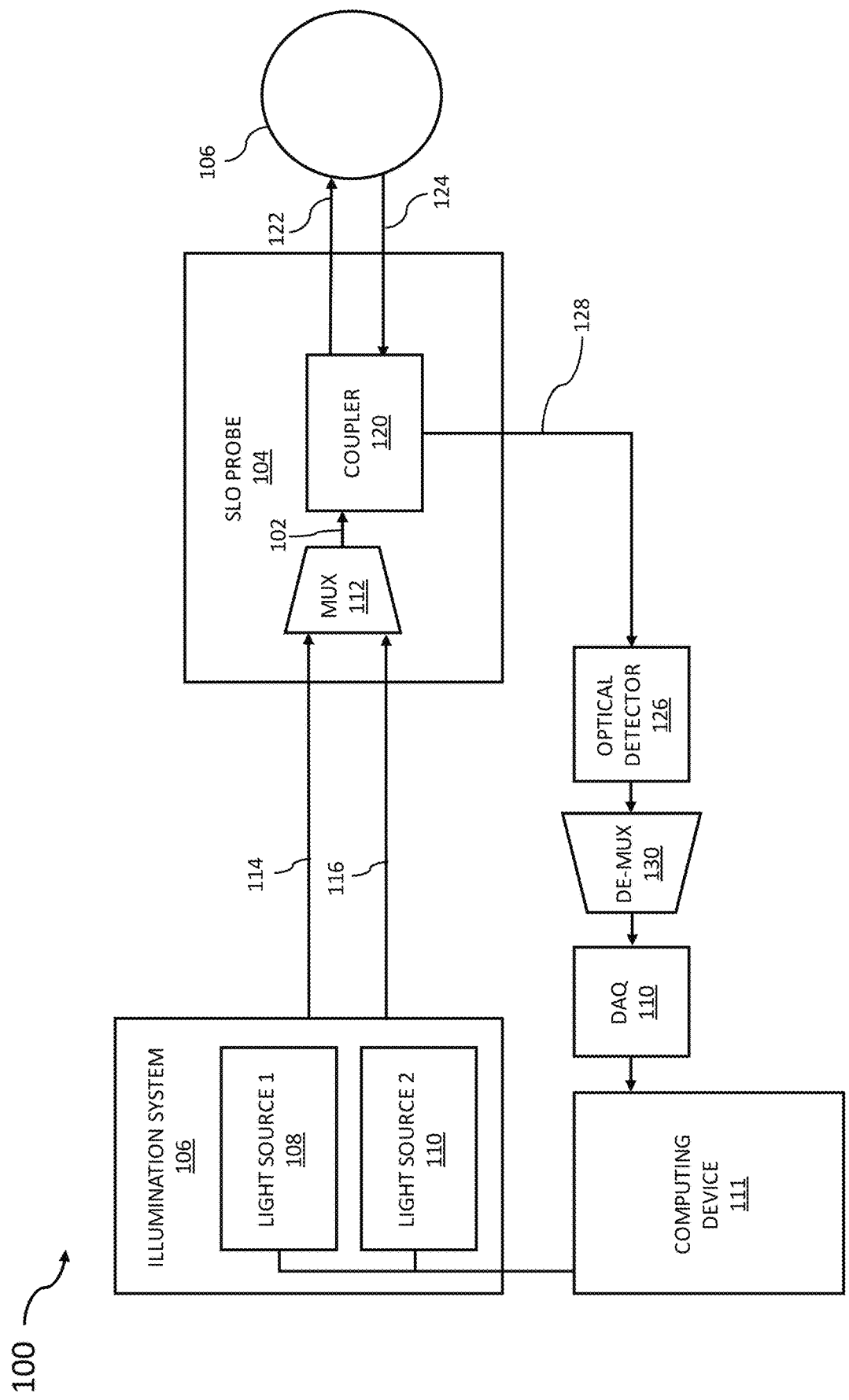
Figure 5A:
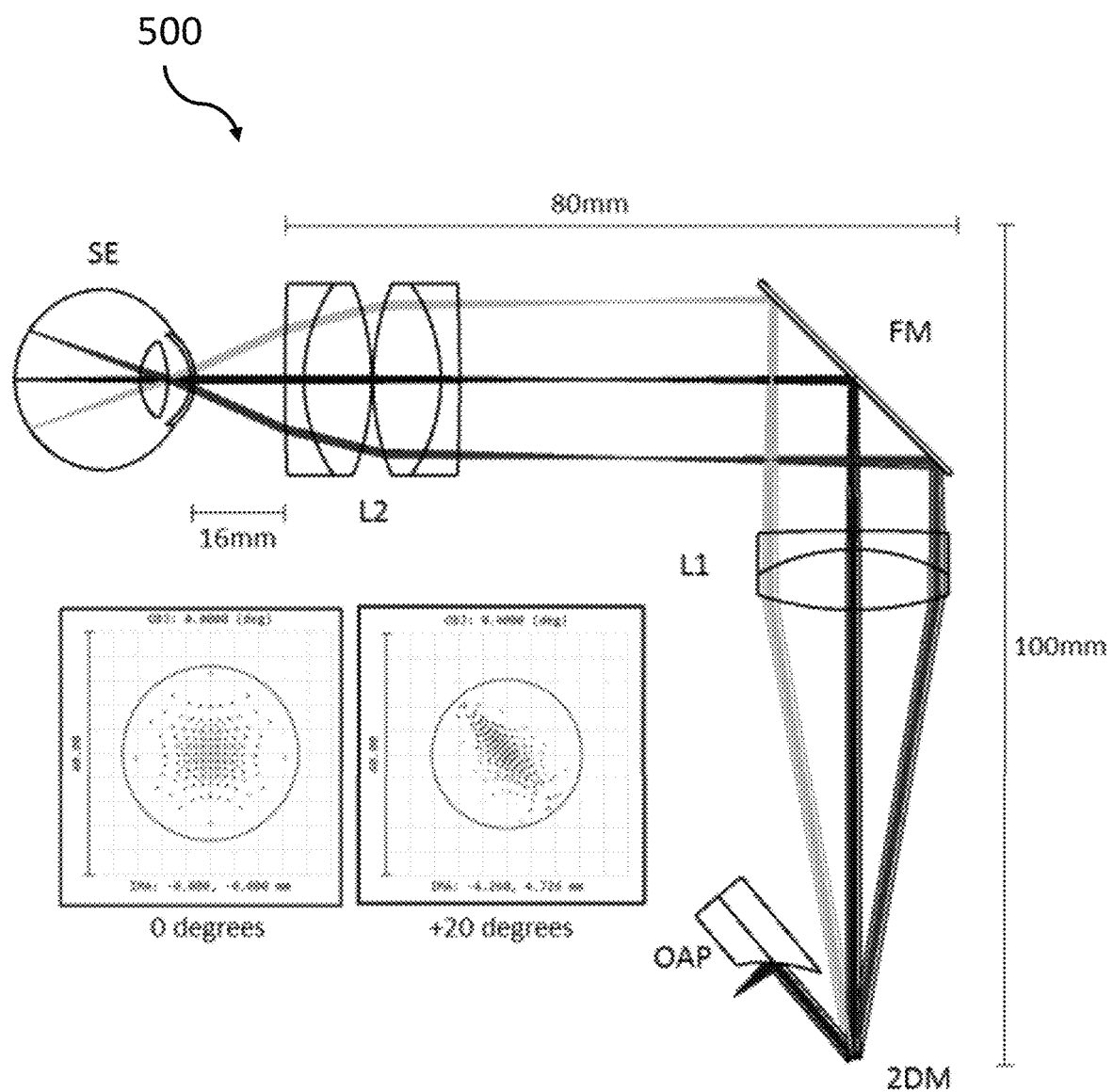
Figure 5B:
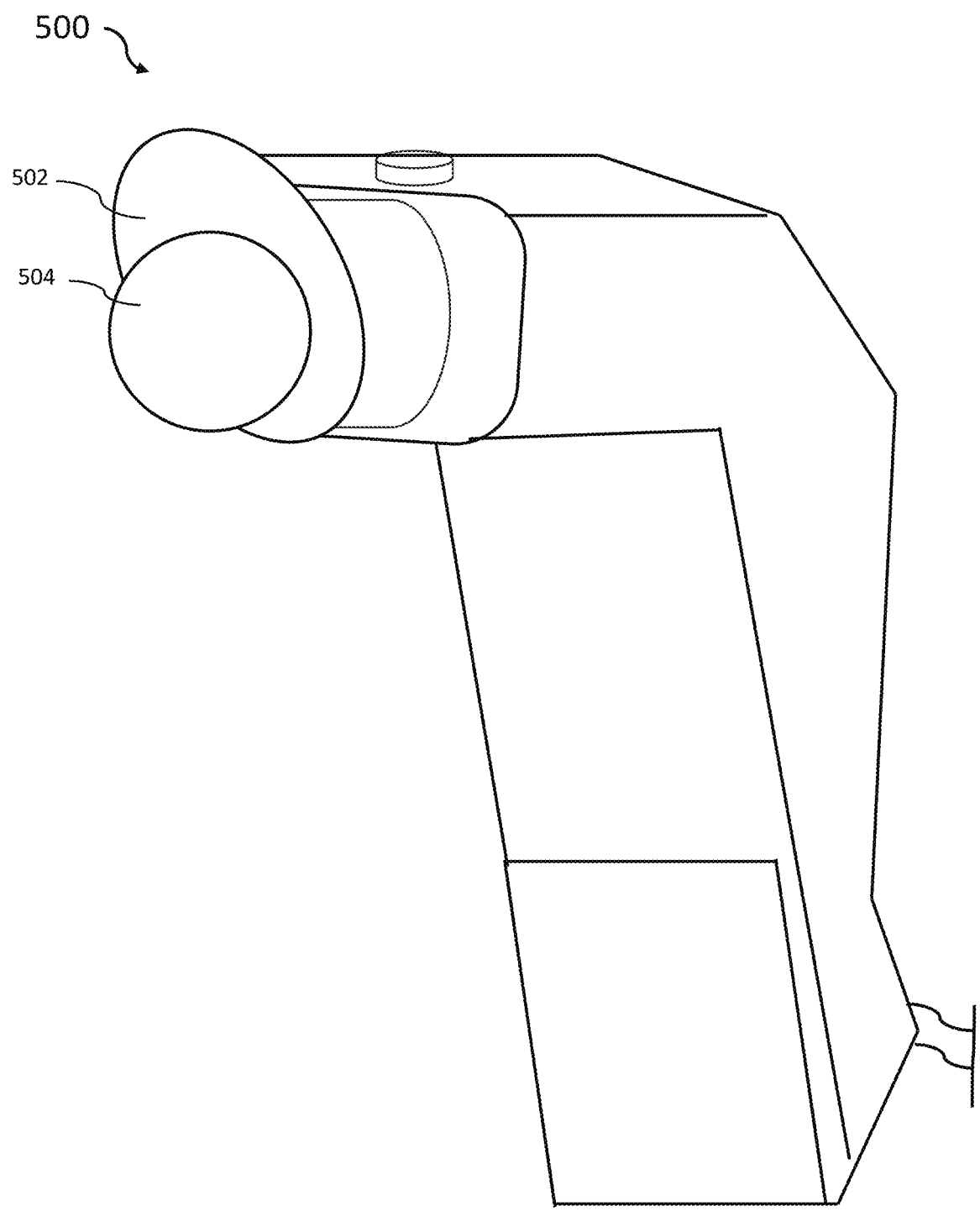
Figure 6:
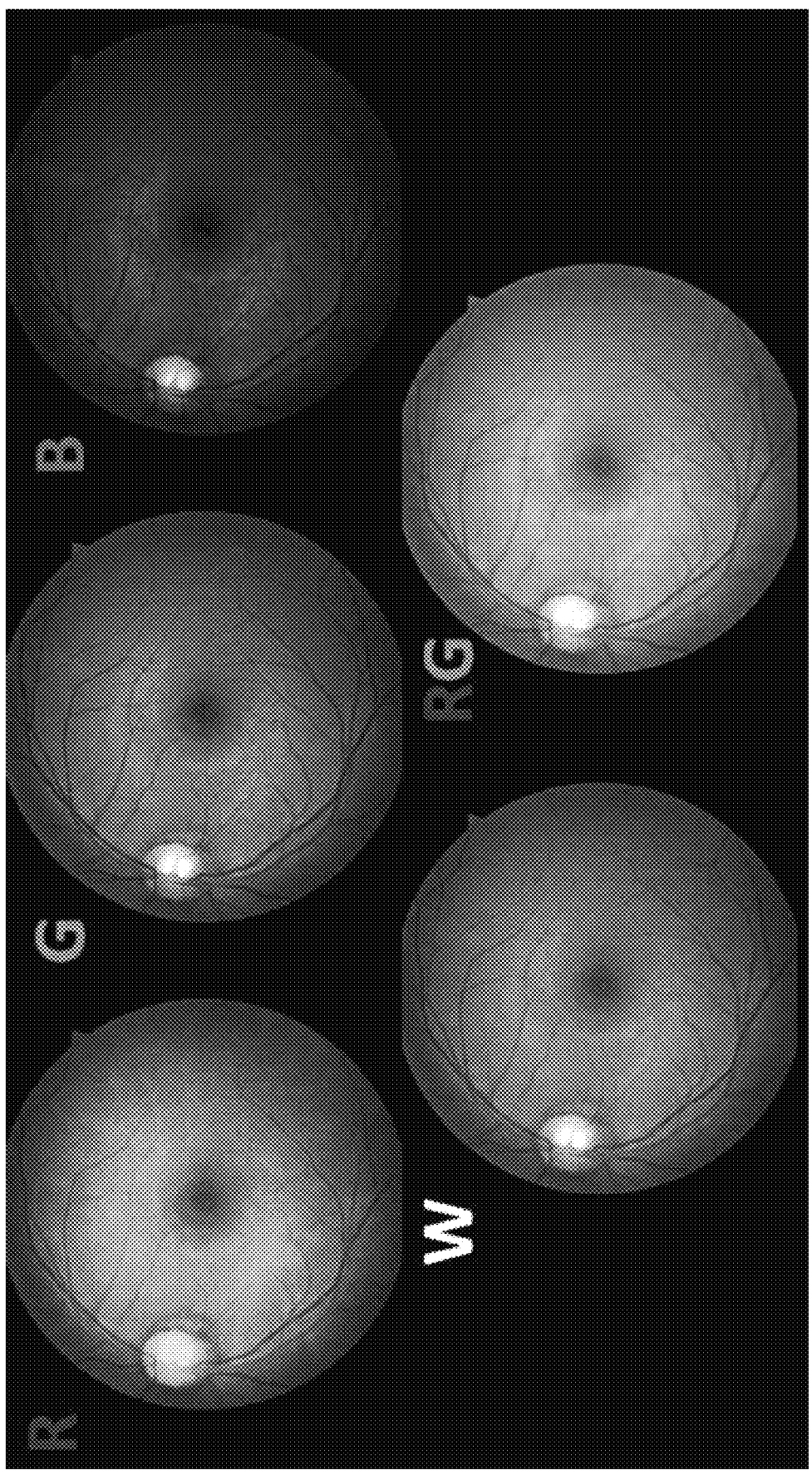
Figure 7:
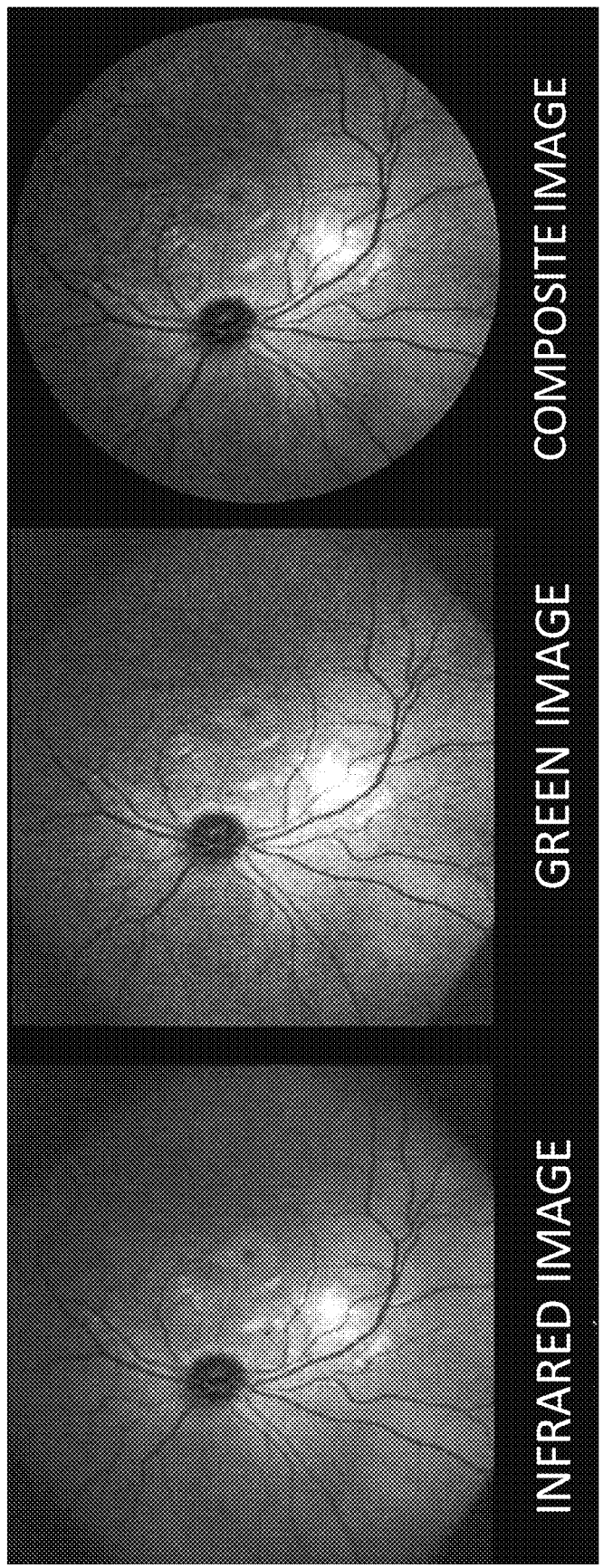

Having thus described the presently disclosed subject matter in general terms, reference will now be made to the accompanying Drawings, which are not necessarily drawn to scale, and wherein:

FIG. 1 is a block diagram of an imaging system configured to multiplex light of different wavelengths onto an input optical channel of an SLO probe for imaging an eye in accordance with embodiments of the present disclosure;

FIG. 2 is a block diagram of another imaging system configured to multiplex light of different frequencies onto an input optical channel of an SLO probe for imaging a subject in accordance with embodiments of the present disclosure;

FIG. 3 is a block diagram of another imaging system configured with a single light source and a tunable filter for alternating light from the illumination system in accordance with embodiments of the present disclosure;

FIG. 4 is a block diagram of another imaging system configured with a MUX positioned within the SLO probe in accordance with embodiments of the present disclosure;

FIG. 5A is a diagram of an optical layer of a cSLO probe that may be used in accordance with embodiments of the present disclosure;

FIG. 5B is a perspective view of the handheld cSLO including an eyecup and a human eye for scale;

FIG. 6 depicts images showing the relative contribution of the three-color channels in a fundus photo; and FIG. 7 depicts example images of retinas acquired with a system in accordance with embodiments of the present disclosure.

SUMMARY

The presently disclosed subject matter provides systems and methods for multiplexing and alternating light of different frequencies in an ophthalmoscope. According to an aspect, an imaging system includes an illumination system configured to generate and output light that alternates between at least two different wavelengths. The imaging system includes a multiplexer configured to receive the output light and to multiplex the light of different wavelengths onto a single optical channel. Further, the imaging system includes a scanning laser ophthalmoscope probe configured to operatively receive the multiplexed light via the optical channel, to apply the multiplexed light to a subject for imaging, and to receive light returning from the subject for generating an image of the subject.

According to another aspect, an imaging system includes a scanning laser ophthalmoscope (SLO). The SLO includes an illumination system configured to generate and output light that alternates between at least two different wavelengths. Further, the SLO includes a probe configured to receive the output light, to apply the light to a subject for imaging, and to receive light returning from the subject for providing image data of the subject. The SLO also includes a computing device configured to use the image data to simulate the image information from the at least one different wavelengths that are not output by the illumination system.

DETAILED DESCRIPTION

The following detailed description is made with reference to the figures. Exemplary embodiments are described to illustrate the disclosure, not to limit its scope, which is defined by the claims. Those of ordinary skill in the art will recognize a number of equivalent variations in the description that follows.

Articles "a" and "an" are used herein to refer to one or to more than one (i.e. at least one) of the grammatical object of the article. By way of example, "an element" means at least one element and can include more than one element.

"About" is used to provide flexibility to a numerical endpoint by providing that a given value may be "slightly above" or "slightly below" the endpoint without affecting the desired result.

The use herein of the terms "including," "comprising," or "having," and variations thereof is meant to encompass the elements listed thereafter and equivalents thereof as well as additional elements. Embodiments recited as "including," "comprising," or "having" certain elements are also contemplated as "consisting essentially of" and "consisting" of those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a range is stated as between 1%-50%, it is intended that values such as between 2%-40%, 10%-30%, or 1%-3%, etc. are expressly enumerated in this specification. These are only examples of what is specifically intended, and all possible combinations of numerical values between and including the lowest value and the highest value enumerated are to be considered to be expressly stated in this disclosure.

Unless otherwise defined, all technical terms used herein have the same meaning as commonly understood by one of ordinary skill in the art to which this disclosure belongs.

FIG. 1 illustrates a block diagram of an imaging system 100 configured to multiplex light of different wavelengths onto an input optical channel 102 of an SLO probe 104 for imaging an eye 106 in accordance with embodiments of the present disclosure. Referring to FIG. 1, the imaging system 100 includes an illumination system 106 configured to function as a source of light for the SLO probe 104. Particularly, the illumination system 106 can generate and output light that alternates between two or more wavelengths. In this example, the illumination system 106 includes two light sources 108 and 110 that generate light of different wavelengths from one another. The system 100 may include a computing device 111 configured to control the light sources 108 and 110 (e.g., activate and deactivate the light sources 108 and 110 by applying or not applying power to the light sources 108 and 110). The light sources 108 and 110 may be of any suitable type such as, but not limited to, laser diodes, superluminescent diodes, light emitting diodes (LEDs), and the like. Also, it is noted that in examples provided herein only two light sources are provided, although any number of light sources may be used.

In accordance with embodiments, the illumination system 106 can alternate the light between two wavelengths. For example, the output light may be alternated between the different wavelengths on a per-pixel basis. In this context, alternating the output light on a per-pixel basis can be that, for each image pixel that is acquired, the illumination system outputs light of each wavelength before the system moves on to the next pixel. This does not require that the scanning mirrors be stationary during the alternating period, or that each output wavelength is incident on precisely the same region of the eye, but only that the alternating of wavelengths occurs on a time-scale similar to that of the time required to acquire a single image pixel.

In another example, the output light may be alternated between the different wavelengths on a per-line basis. In this context, alternating the output light on a per-line basis means that, for each image line that is acquired, the illumination system outputs light of each wavelength before the system moves on to the next line. This does not require that, for a given line, each output wavelength is incident on precisely the same region of the eye, as embodiments where adjacent lines are acquired with alternating wavelengths can be realized. Broadly, per-line basis can mean that the alternating of wavelengths occurs on a time-scale similar to that of the time required to acquire a single image line. The term "line" in this context does not necessarily mean a one-dimensional scan path. Rather, line may also refer to any short acquisition consisting of multiple pixels, including but not limited to, segments of a spiral, concentric circles, or small, irregularly shaped areas.

In another example, the output light may be alternated between the different wavelengths on a per-frame basis. In this context, alternating the output light on a per-frame basis means that one or more full frames are acquired at each wavelength before the light output changes to the next wavelength in the sequence. There is no requirement that integer number of frames be acquired before alternating. The system may alternate between wavelengths after acquiring any number frame of frames, including non-integer numbers of frames including partial frames.

Additional embodiments, where the output light alternates wavelengths after acquiring different image region shapes and sizes, such as rectangular regions, concentric circles or segments of a spirals, can also be conceived of.

In another example and alternative to the two light sources 108 and 110, the illumination system 106 may include a broadband light source. The broadband light source may be suitably filtered to produce illumination at multiple narrow wavelength bands. In an example, the broadband light source may be a thermal light source such as, but are not limited to, a halogen lamp, a tungsten halogen lamp, a quartz-halogen lamp, a quartz iodine lamp, or the like. In another example, the broadband light source may be a broadband laser such as, but not limited to, a short-pulse laser, or a supercontinuum source, or the like.

The output light of the illumination system 106 may include light of various wavelengths for application to the eye 106 for imaging. In an example, the output light may include light of an infrared illumination wavelength for aligning the probe or another optical system on the eye 106 or another subject. In another example, the output light may include light of an infrared illumination wavelength for simulating the subject's (e.g., the eye's) response to a red illumination wavelength.

In another example, output light of the illumination system can include light of a green wavelength and an infrared wavelength. An optical detector (e.g., optical detector 126 as will be described in further detail herein) can detect returning light of the green wavelength and the infrared wavelength for simulating the subject's response to white light illumination. The computing device 111 can estimate the subject response to the white light illumination.

In another example, output light of the illumination system can include light of a green wavelength and red wavelength. An optical detector (e.g., optical detector 126 as will be described in further detail herein) can detect returning light of the green wavelength and the red wavelength for simulating the subject's response to white light illumination.

The computing device 111 can estimate the subject response to the white light illumination.

In another example, output light of the illumination system can include light of a green wavelength. An optical detector (e.g., optical detector 126 as will be described in further detail herein) can detect returning light of the green wavelength for simulating the subject's response to blue light illumination. The computing device 111 can estimate the subject response to the blue light illumination.

Outputs of the light sources 108 and 110 may be operatively connected to inputs of a multiplexer (MUX) 112 via optical fibers 114 and 116, respectively. Example optical fibers include, but are not limited to, single mode optical fibers, multi-mode optical fibers, dual-clad optical fibers, and the like, and combinations thereof. The optical fibers 114 and 116 may provide channels for transmitting the light of different wavelengths to the MUX 112. The MUX 112 may be configured to temporally multiplex the light of different wavelengths. For example, the MUX 112 may temporally multiplex the light by modulating drive currents to the light sources. An output of the MUX 112 multiplexes the received light onto a single optical channel 118, which is received by a coupler 120. The coupler 120 may be a double clad fiber coupler, a polarizing beamsplitter, a non-polarizing beamsplitter, or any other suitable coupler. The coupler 120 may split and combine the illumination and collection channels of the probe 104. Further, the coupler 120 may pass the multiplexed light to the input optical channel 102 for receipt by the SLO probe 104.

The SLO probe 104 may be suitably operated by its operator to apply the received light 122 to the eye 106, such as application to a retina of the eye 106. The optical fiber 102 may be, for example, dual-clad optical fiber having multiple channels, delivered and returning, collected light may be via either channel of the dual-clad optical fiber. Further, the SLO probe 104 may receive light from the eye 106 and return the light 124 via channel 102 to the coupler 120. The coupler 120 may direct the returned light 124 to an optical detector 126 via an optical fiber 128. The optical detector 126 is configured to detect the light 124 returning from the eye 106 and generate a signal representative of the light 124. Example optical detectors include, but are not limited to, an avalanche photodiode, a photomultiplier tube, a photodiode, and the like.

The output signal of the optical detector 126 may be transmitted to a de-multiplexer (DE-MUX) 130 configured to temporally de-multiplex the returning signal to isolate each wavelength carried by the signal. Output of the DE-MUX 130 may be received by a data acquisition (DAQ) module 132 for processing and conditioning prior to receipt by the computing device 111. The computing device 111 may receive the data in suitable form for generating images of the eye (e.g., the retina). The images may be presented by a user interface (e.g., a display) of the computing device 111 and/or suitably stored at the computing device 111.

In embodiments, the light returning from the eye 106 may be collected in a multi-mode optical fiber for relay to the optical detector 126. Alternatively, for example, the light returning from the eye 106 may be collected in a single mode optical fiber for relay to the optical detector 126. In another example, the light returning from the eye 106 may be directly detected on an optical detector 126 without passing through an optical fiber. Such a "direct detection" scheme may include a pinhole configured to receive and pass light returning before being directly detected by the optical detector 126, but is not necessarily required to include a pinhole.

In an embodiment, the system 100 may include a non-polarizing beamsplitter cube configured to split and combine the illumination and collection channels of the probe 106. In another example, the system 100 may include a polarizing beamsplitter cube configured to split and combine the illumination and collection channels of the probe 106. In another example, the system 100 may include a dual-clad optical fiber configured to split and combine the illumination and collection channels of the probe 106 through the single-mode and multi-mode channels of the dual-clad optical fiber. In another example, one or more of the wavelengths are shorter than the single mode cut-off of the single-mode fiber of a dual clad optical fiber.

In accordance with embodiment, an imaging system, such as the imaging system 100 shown in FIG. 1, can use image data to simulate image information from one or more different wavelengths that are not output by the illumination system. For example, the illumination system 106 can generate and output light that alternates between two or more wavelengths. The probe 104 can receive the output light, apply the light to a subject for imaging, and receive light returning from the subject (e.g., the eye 106) for providing imaging data of the subject. Further, the computing device 111 can use the image data to simulate the image information from the different wavelengths that are not output by the illumination system.

Various methods and algorithms can be used to compute simulated image data from wavelengths not output by the illumination system. These methods may employ untrained algorithms, wherein the response to one or more wavelengths are inputs to an equation, the outputs of which are the simulated response to one or more different wavelengths. These equations may include, but are not limited to, linear or polynominal spectral weighting functions or spectral interpolation functions.

In embodiments of this technique, image data from an infrared channel can be mapped to a red channel using a coefficient of unity. Further, image data from a green channel can be mapped to a green channel using a coefficient of unity and to a blue channel using a coefficient of between approximately 0.05 and 0.2. The resulting RBG image is the output of the system.

Simulated image data from wavelengths not output by the illumination system can also be computed through trained computational systems. These system take, as inputs, training images acquired at one or more wavelengths output by the illumination system, and images acquired at wavelengths not output by the illumination system. Training images may be, but are not required to be, acquired from a different imaging modality, such as fundus photography. The system then employ various algorithms and training methods, including but not limited to machine learning techniques, artificial intelligence, convolutional neural networks, deep learning systems, or any other training technique. Once trained, the computational system takes as inputs image of a subject acquired at one or more wavelengths output by the illumination system, and returns as output simulated images of the subject at one or more different wavelengths.

In an example of this technique, a training set of red-green-blue (RGB) fundus photos and infrared and green SLO images are used to train a convolutional neural network (CNN). Once trained, the CNN will take, as inputs, infrared and green SLO images and return simulated RBG images.

In an example the output light of the illumination system 106 includes light of an infrared illumination wavelength, and the optical detector 126 detects returning light for simulating the subject's response to a red illumination wavelength estimate. In another example the output light of the illumination system 106 includes light of a green illumination wavelength, and the optical detector 126 detects returning light for simulating the subject's response to a red illumination wavelength. In another example the output light of the illumination system 106 includes light of a green illumination wavelength and an infrared illumination wavelength, and the optical detector 126 detects returning light for simulating the subject's response to a white illumination wavelength. In another example the output light of the illumination system 106 includes light of a green illumination wavelength and an infrared illumination wavelength, and the optical detector 126 detects returning light for simulating the subject's response to a red, green and blue illumination wavelength. In another example the output light of the illumination system 106 includes light of a green illumination wavelength and a red illumination wavelength, and the optical detector 126 detects returning light for simulating the subject's response to a white light (broadband) illumination wavelength. In another example the output light of the illumination system 106 includes light of a green illumination wavelength and a red illumination wavelength, and the optical detector 126 detects returning light for simulating the subject's response to a red, green and blue illumination wavelength.

FIG. 2 illustrates a block diagram of another imaging system 200 configured to multiplex light of different wavelengths onto an input optical channel 102 of an SLO probe 104 for imaging a subject in accordance with embodiments of the present disclosure. This figure depicts a system topology and time-division spectral multiplexing technique for imaging the subject (e.g., an eye's retina). The system 200 includes two light sources: a laser diode (LD) 202 and a superluminescent diode (SLD) 204. In an example, the LD 202 generates and outputs light having a 532 nm wavelength. In examples, the LD 202 may operate between about 500 nm and 565 nm (e.g., at a wavelength suitable for green illumination). Further, for example, the SLD 204 generates and output light having a 780 nm wavelength. In examples, the SLD 204 may operate between about 600 nm and about 900 nm (e.g, at 600 nm, 650 nm, 700 nm, 750 nm, 780 nm, 800 nm, 850 nm, or 900 nm). The system 200 includes a wavelength division multiplexer (WDM) 206 that receives the light output by the LD 202 and SLD 204. The LD 202 and the SLD 204 may each be coupled to the WDM 206 via a single mode optical fiber. The SLD 204 is for NIR illumination. It is noted that any suitable number and type of fiber-coupled light sources may be used.

The LD 202 and the SLD 204 may be activated by current drivers that are controlled by a personal computer and data acquisition (DAQ) system 208. In accordance with embodiments, the current drivers for the LD 202 and the SLD 204 are driven by square waves. In an example, the current drive is drive by two 5 MHz square waves that are 180 degrees out of phase. As an alternative to achieving time multiplexing through modulating the diode current drivers, the output of any two (or more) continuous-wave (CW) light sources may be alternated similarly through suitable use of readily available optical modulators or switches. The two light sources in the embodiment shown in FIG. 2 are combined via WDM 206, producing an optical signal rapidly switching between light sources (in this case green and NIR) with nearly 100% combined duty cycle. The combined output is subsequently directed towards the handheld SLO probe via a single mode (SM) fiber 210. In embodiments, the SM fiber 210 is part of a double clad fiber coupler (DCFC) 212. Returning light is collected in the multimode portion 216 of the double clad fiber (DCF) 214. It should be understood that while DCF is well suited for the systems provided herein, other topologies can be envisioned using separated single mode and multimode fibers, or even directly coupling the return light to the detector. Returning light can be detected with a single avalanche photodiode (APD) 218, then digitized using a 10 MHz clock phase-locked to the 5 MHz square waves. The PC and DAQ system 208 may then process the digitized data to generate image data of the subject suitable for display to a user.

FIG. 3 illustrates a block diagram of another imaging system 100 configured with a single light source 300 and a tunable filter 302 for alternating light from the illumination system 100 in accordance with embodiments of the present disclosure. The system 100 of FIG. 3 is similar to the system 100 of FIG. 1 except that it has a single light source 300 within the illumination system 106, and it has the tunable filter 302. The single light source 300 can generate light 114 of any wavelength within a broad spectral band. In an example, this light source is a supercontinuum light source, capable of emitting light between 400 nm and 2400 nm. The tunable filter 302 can receive the generated light 114 and filter it to produce a narrow spectral band light output. The passband of this filter can be modulated to produce light output alternating between two or more wavelengths. In an example, this filter is an acousto-optic tunable filter. The output of the tunable filter 302 can be received by the coupler 120 for further processing in accordance with examples described herein.

FIG. 4 illustrates a block diagram of another imaging system configured with the MUX 112 positioned within the SLO probe 104 in accordance with embodiments of the present disclosure. The system 100 of FIG. 4 is similar to the system 100 of FIG. 1 except that the MUX 112 is positioned within the SLO probe.

In embodiments, the MUX can be a dichroic mirror or a system of dichroic mirrors, that directs two or more wavelengths to be incident on the scanning mirror (or, if a pair of scanning mirrors is used, either the first or the second scanning mirror) at the same position and the same angle. After relaying through the SLO probe optics, the beams corresponding to each wavelength will be incident on the subject pupil plane at largely the same position and same angle.

In other embodiments, the MUX may be an arrangement of optics by that directs two or more wavelengths to be incident on the scanning mirror (or, if a pair of scanning mirrors is used, either the first or the second scanning mirror) at the same angle but at different positions on the mirror. After relaying through the SLO probe optics, the beams corresponding to each wavelength can be incident on the subject pupil plane at either the same angle but different positions, or at different positions but at the same angle.

In other embodiments, the MUX may be an arrangement of optics by which two or more wavelengths are incident on the scanning mirror (or, if a pair of scanning mirrors is used, either the first or the second scanning mirror) at different angles, but at the same position on the mirrors. After relaying through the SLO probe optics, the beams corresponding to each wavelength will be incident on the subject pupil plane at either the same angle but different positions, or at different positions but at the same angle.

In other embodiments, the MUX can be a system by which two or more wavelengths are incident on the scanning mirror (or, if a pair of scanning mirrors is used, either the first or the second scanning mirror) at the different angles and at different positions on the mirror. After relaying through the SLO probe optics, the beams corresponding to each wavelength will be incident on the subject pupil plane at different positions and angles.

In accordance with embodiments, a confocal scanning laser ophthalmoscope (cSLO) probe may be used with imaging systems described herein. FIG. 5A illustrates a diagram of an optical layout of a cSLO probe 500 that may be used in accordance with embodiments of the present disclosure. For example, the cSLO probe 500 may be used in place of the SLO probes shown in FIGS. 1 and 2. Referring to FIG. 5A, this design can achieve a 40° field-of-view (FOV) at a working distance of 16 mm. The system can achieve diffraction limited performance of the subject eye across the entire 40° FOV (spot diagrams are shown in the inset of FIG. 5A). In FIG. 5A, OAP represents off axis parabolic mirror, 2DM represents two dimensional MEMS mirror, L1 represents telecentric lens, FM represents fold mirror, L2 represents Plossl eyepiece, and SE represents subject eye. FIG. 5B illustrates a perspective view of the handheld cSLO 500 including an eyecup 502 and a human eye 504 for scale.

As described herein, the combination of NIR and green wavelength light illumination may be utilized for simulating a subject's response to white light. Green wavelength light been shown to carry the most vessel contrast. NIR light may be selected as a surrogate for a red channel, providing nearly identical information while further reducing the miotic response and scattering from cataracts. In some cases, no blue channel is included, as the blue light carries limited information about the retinal vasculature and poses the highest risk of phototoxicity. To illustrate the information contribution of each color channel, the channels of a standard fundus photo may be separated from a tabletop digital fundus camera. For example, FIG. 6 depicts images showing the relative contribution of the three-color channels in a fundus photo (R represents red, G represents green, B represents blue; W represents red, green, and blue channels combined; RG represents red and green channels combined). The red, green and blue channels are shown in the top row of FIG. 6, illustrating the superficial nature of the information content in the blue channel relative to red and green. The second row of FIG. 6 juxtaposes the original image (W) and a combination of only the red and green channels (RG). The similarity of information between these two images further emphasizes the redundancy of information in the blue channel.

In accordance with embodiments, an infrared illumination source (in an example, an 810 nm superluminescent diode) and a green illumination source (in an example, a 520 nm green laser diode) can be combined via a wavelength division multiplexer and relayed to an SLO probe via a single mode optical fiber. The illumination and collection channels can be multiplexed via a non-polarizing beamsplitter, and light returning from the subject can be collected on a multi-mode fiber and detected on a photomultiplier tube. The infrared and green illumination sources can alternate on either a per-line or per-frame basis. Image acquisition may include aiming with the infrared illumination source only, and then illuminating with the alternative infrared and green illumination pattern. Signals collected by the photomultiplier tube are assigned to their correct illumination color channel (green or infrared). Green image information can be used to simulate response to blue illumination, and infrared image information can be used to simulate response to red illumination. An estimate of a white light image can subsequently be computed based on the estimated blue, measured green and estimated red color information. FIG. 7 depicts example images of retinas acquired with a system in accordance with embodiments of the present disclosure.

The present subject matter may be a system, a method, and/or a computer program product. The computer program product may include a computer readable storage medium (or media) having computer readable program instructions thereon for causing a processor to carry out aspects of the present subject matter.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a RAM, a ROM, an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network, or Near Field Communication. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present subject matter may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++, Javascript or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present subject matter.

Aspects of the present subject matter are described herein with reference to flowchart illustrations and/or block diagrams of methods, apparatus (systems), and computer program products according to embodiments of the subject matter. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present subject matter. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the embodiments have been described in connection with the various embodiments of the various figures, it is to be understood that other similar embodiments may be used, or modifications and additions may be made to the described embodiment for performing the same function without deviating therefrom. Therefore, the disclosed embodiments should not be limited to any single embodiment, but rather should be construed in breadth and scope in accordance with the appended claims.

What is claimed is:

1. An imaging system comprising:
   an illumination system configured to output light that alternates between at least two different wavelengths;
   a multiplexer configured to receive the output light and to multiplex the light of different wavelengths onto a single optical channel; and
   a scanning laser ophthalmoscope probe configured to operatively receive the multiplexed light via the optical channel, to apply the multiplexed light to a subject for imaging, and to receive light returning from the subject for generating an image of the subject.

2. The system of claim 1, wherein the illumination system is configured to alternate the output light between the at least two different wavelengths on a per-pixel basis.

3. The system of claim 1, wherein the illumination system is configured to alternate the output light between the at least two different wavelengths on a per-line basis.

4. The system of claim 1, where the illumination system is configured to alternate the output light between the at least two different wavelengths on a per-frame basis.

5. The system of claim 1, wherein the illumination system is configured to alternate the output light while scanning shapes including one of spirals, concentric circles, or arbitrarily-shaped areas.

6. The system of claim 1, wherein the illumination system comprises a plurality of light sources configured to generate and output the light of the at least two different wavelengths.

7. The system of claim 6, wherein the light sources include one or more laser diodes, superluminescent diodes, or light emitting diodes.

8. The system of claim 6, wherein the light sources are operatively coupled to single mode optical fibers.

9. The system of claim 6, wherein the light source are operatively coupled to multi-mode optical fibers.

10. The system of claim 6, wherein the light sources are operatively coupled to a combination of single-mode, multi-mode optical fibers, or dual-clad optical fibers.

11. The system of claim 1, wherein the illumination system comprises a broadband light source that is filtered to produce illumination at multiple narrow wavelength bands.

12. The system of claim 11, wherein the broadband light source is one or more of a halogen lamp, a tungsten halogen lamp, a quartz-halogen lamp, or quartz iodine lamp.

13. The system of claim 11, wherein the broadband light source is one or more of a broadband laser, short-pulse laser or supercontinuum source.

14. The system of claim 1, wherein the illumination system comprises a plurality of light sources configured to generate the output light, and
   wherein the multiplexer is configured to temporally multiplex the light by modulating drive currents to the light sources.

15. The system of claim 1, wherein the illumination system is a filtered broadband illumination system, and
   wherein the multiplexer is configured to temporal multiplex by modulating a passband of the filtered broadband illumination system.

16. The system of claim 1, further comprising a single optical detector configured to detect the light returning from the subject, and wherein the imaging system further comprises a de-multiplexer configured to temporally de-multiplex the returning signal to isolate each wavelength.

17. The system of claim 16, wherein the optical detector is an avalanche photodiode.

18. The system of claim 16, wherein the optical detector is a photomultiplier tube.

19. The system of claim 16, wherein the optical detector is a photodiode.

20. The system of claim 1, wherein the output light comprises light of an infrared illumination wavelength for aligning an optical system on the subject.

21. The system of claim 1, wherein the output light comprises light of an infrared illumination wavelength for simulating the subject's response to a red illumination wavelength.

22. The system of claim 1, wherein the output light includes light of a green wavelength and an infrared wavelength, and
wherein the system further comprises an optical detector configured to detect returning light of the green wavelength and the infrared wavelength for simulating the subject's response to white light illumination.

23. The system of claim 1, wherein the output light includes light of a green wavelength and a red wavelength, and
wherein the system further comprises an optical detector configured to detect returning light of the green wavelength and the red wavelength for simulating the subject's response to white light illumination.

24. The system of claim 22, wherein the output light includes light of a green wavelength, and
wherein the system further comprises an optical detector configured to detect returning light of the green wavelength for simulating the subject's response to a blue illumination wavelength.

25. The system of claim 1, further comprising a dual-clad optical fiber having multiple channels, and
wherein the light is delivered to the scanning laser ophthalmoscope probe via either channel of the dual-clad optical fiber.

26. The system of claim 1, further comprising a dual-clad optical fiber having multiple channels, and
wherein the light returning from the subject is collected in either channel of the dual-clad optical fiber for relay to an optical detector.

27. The system of claim 1, wherein the light is delivered to the scanning laser ophthalmoscope probe via a single mode channel of a dual-clad optical fiber, and light returning from the subject is collected in a multi-mode channel of the same dual-clad optical fiber for relay to an optical detector.

28. The system of claim 1, wherein the light returning from the subject is collected in a multi-mode optical fiber for relay to an optical detector.

29. The system of claim 1, wherein the light returning from the subject is collected in a single mode optical fiber for relay to an optical detector.

30. The system of claim 1, further comprising a pinhole configured to receive and pass the light returning before being directly detected on an optical detector.

31. The system of claim 1, further comprising a non-polarizing beamsplitter cube configured to split and combine the illumination and collection channels of the scanning laser ophthalmoscope probe.

32. The system of claim 1, further comprising a polarizing beamsplitter cube configured to split and combine the illumination and collection channels of the scanning laser ophthalmoscope probe.

33. The system of claim 1, further comprising a dual-clad optical fiber configured to split and combine the illumination and collection channels of the SLO probe through the single-mode and multi-mode channels of the dual-clad optical fiber.

34. The system of claim 26, wherein one or more of the wavelengths are shorter than the single mode cut-off of the single-mode fiber of a dual clad optical fiber.

35. A scanning laser ophthalmoscope comprising:
an illumination system configured to output light that alternates between at least two different wavelengths;
a probe configured to receive the output light, to apply the light to a subject for imaging, and to receive light returning from the subject for providing image data of the subject; and
a computing device configured to use the image data to simulate the image information from the at least one different wavelengths that are not output by the illumination system.

36. The system of claim 35, wherein the output light includes light of an infrared illumination wavelength, and
wherein the system further comprises an optical detector configured to detect the returning light for simulating the subject's response to a red illumination wavelength.

37. The system of claim 35, wherein the output light includes light of a green wavelength, and
wherein the system further comprises an optical detector configured to detect the returning light for simulating the subject's response to a blue illumination wavelength.

38. The system of claim 35, wherein the output light includes light of a green wavelength and an infrared wavelength, and
wherein the system further comprises an optical detector configured to detect the returning light for simulating the subject's response to white light illumination.

39. The system of claim 35, wherein the output light includes light of a green wavelength and an infrared wavelength, and
wherein the system further comprises an optical detector configured to detect the returning light for simulating the subject response to red, green and blue illumination.

40. The system of claim 35, wherein the output light includes light of a green wavelength and a red wavelength, and
wherein the system further comprises an optical detector configured to detect the returning light for simulating the subject's response to white light (broadband) illumination.

41. The system of claim 35, wherein the output light includes light of a green wavelength and a red wavelength, and
wherein the system further comprises an optical detector configured to detect the returning light for simulating the subject's response to red, green and blue illumination.

42. An imaging system comprising:
an illumination system configured to output light that alternates between at least two different wavelengths;
a scanning laser ophthalmoscope probe configured to operatively deliver the at least two different wavelengths to a subject for imaging, and to receive light returning from the subject for generating an image of the subject; and a multiplexer configured to receive the light returning from the subject, and to multiplex the light of different frequencies onto a single optical detection channel.

43. The system of claim 42, wherein, for any scan position, the different wavelengths are incident on the subject eye at nominally the same location in the pupil, but with varying incident angles at the pupil.

44. The system of claim 42, wherein, for any scan position, the different wavelengths are incident on the subject eye at the same incident angle at the pupil, but with varying locations within the pupil.

45. The system of claim 42, wherein, for any scan position, the different wavelengths are incident on the subject eye at the same incident angle at the pupil, and at the same location within the pupil.

* * * * *